United States Patent
Ohta et al.

(10) Patent No.: US 10,033,739 B2
(45) Date of Patent: Jul. 24, 2018

(54) CLINICAL-PATH MANAGEMENT SERVER AND CLINICAL-PATH MANAGEMENT SYSTEM

(71) Applicant: FUJIFILM Corporation, Tokyo (JP)

(72) Inventors: Yasunori Ohta, Ashigarakami-gun (JP); Satoshi Ueda, Tokyo (JP); Yuya Kudo, Tokyo (JP); Hironori Matsumasa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 204 days.

(21) Appl. No.: 15/080,889

(22) Filed: Mar. 25, 2016

(65) Prior Publication Data
US 2016/0212135 A1    Jul. 21, 2016

Related U.S. Application Data

(63) Continuation of application No. PCT/JP2014/074462, filed on Sep. 17, 2014.

(30) Foreign Application Priority Data

Sep. 27, 2013   (JP) .................. 2013-201505

(51) Int. Cl.
*H04L 29/06*    (2006.01)
*G06Q 50/22*    (2018.01)
(Continued)

(52) U.S. Cl.
CPC ......... *H04L 63/10* (2013.01); *G06Q 10/0631* (2013.01); *G06Q 50/22* (2013.01);
(Continued)

(58) Field of Classification Search
CPC ... H04L 63/10; G06F 19/322; G06F 19/3425; G06Q 10/0631; G06Q 50/22
See application file for complete search history.

(56) References Cited

U.S. PATENT DOCUMENTS

| 2012/0022885 A1* | 1/2012 | Murayama | G06F 19/327 705/2 |
| 2012/0116800 A1* | 5/2012 | McCallie | G06Q 10/10 705/2 |
| 2014/0081659 A1* | 3/2014 | Nawana | A61B 5/0022 705/3 |

FOREIGN PATENT DOCUMENTS

JP    2008-59316 A    3/2008

OTHER PUBLICATIONS

International Search Report for PCT/JP2014/074462 (PCT/ISA/210) dated Oct. 21, 2014.

(Continued)

*Primary Examiner* — Oleg Korsak
(74) *Attorney, Agent, or Firm* — Birch, Stewart, Kolasch & Birch, LLP (57) ABSTRACT

A request distribution unit, an SO acquisition request reception unit, a creation request issuance unit, and an authorization unit are added to the clinical-path management server. The request distribution unit distributes an SO acquisition request and an access request for access to a CP. The SO acquisition request reception unit receives an SO acquisition request from a patient terminal. The creation request issuance unit issues an SO creation request to an SO attending doctor responsible for an SO. When the creation request is issued, the authorization unit grants editing authority to edit the CP of the patient requesting the SO. The authorization unit grants editing authority by updating authority management information stored in an authority management information storage unit.

9 Claims, 10 Drawing Sheets

(51) Int. Cl.
*G06Q 10/06* (2012.01)
*G16H 80/00* (2018.01)
*G16H 10/60* (2018.01)

(52) U.S. Cl.
CPC ............. *G16H 10/60* (2018.01); *G16H 80/00* (2018.01); *H04L 63/08* (2013.01)

(56) References Cited

OTHER PUBLICATIONS

Written Opinion of the International Searching Authority for PCT/JP2014/074462 (PCT/ISA/237) dated Oct. 21, 2014.

* cited by examiner

<ACQUISITION REQUEST PROCESS>

FIG. 10

CLINICAL-PATH MANAGEMENT SERVER AND CLINICAL-PATH MANAGEMENT SYSTEM

CROSS-REFERENCE TO RELATED APPLICATIONS

This application is a Continuation of PCT International Application No. PCT/JP2014/074462 filed on Sep. 17, 2014, which claims priority under 35 U.S.C § 119(a) to Japanese Patent Application No. 2013-201505 filed Sep. 27, 2013. The above application is hereby expressly incorporated by reference, in its entirety, into the present application.

BACKGROUND OF THE INVENTION

1. Field of the Invention

The present invention relates to a clinical-path management server and a clinical-path management system that manage a clinical path in which medical care information of a patient is recorded.

2. Description Related to the Prior Art

In the medical field, a clinical-path management system including a clinical-path management server that manages a clinical path in which medical care information of a patient has been recorded, and a terminal capable of accessing the clinical-path management server is known (see JP2008-059316A). The clinical path is medical care schedule data in which medical care information on a schedule and a record of medical care (diagnosis and treatment) performed on a patient has been recorded in time series. The medical care information includes a schedule of medical care activity such as tests, medical examination, surgery, or medication, and results or records of the medical care activity such as a test result, a medical examination record, and a medication result. Further, since the clinical path is information created for each patient, patient information such as a name, an age, and a gender of the patient, or a name or an Identification Data (ID) of an attending doctor responsible for the patient, and the like are recorded in the clinical path.

The clinical path management server described in JP2008-059316A receives an access from a terminal of an attending doctor, a nurse, or the like, and permits the terminal to view or edit the clinical path. Further, the clinical path management server also receives an access from a terminal of a patient such that the patient can view the clinical path. The patient can recognize details of content of medical care and a policy of the medical care by viewing the clinical path.

Further, the clinical-path management server of JP2008-059316A has a function of requesting a doctor other than the attending doctor to provide a second opinion for the content of medical care which is an opinion of a doctor other than the attending doctor in a case in which the patient wants to acquire a second opinion. The patient can use the second opinion to determine whether or not the medical care policy of the current attending doctor is appropriate.

If the clinical path management server in JP2008-059316A receives a request for acquisition of the second opinion from the patient, the clinical path management server transmits patient information and request information to a doctor who is a request destination of the second opinion to perform a request for creation of the second opinion. When the request information is transmitted, information on the clinical path of the patient is attached, if necessary. The doctor who is the request destination can recognize content of medical care of the patient to date or a future care plan by referring to an electronic medical record or the clinical path, to create the second opinion.

If the second opinion is created, data of the created second opinion is transmitted from the doctor who is a request destination to the clinical-path management server. If the clinical path management server receives the second opinion, the clinical path management server distributes the clinical path created by the attending doctor and the second opinion to a terminal of the patient such that the clinical path and the second opinion can be contrasted with each other. Further, the second opinion can be distributed to the attending doctor if the patient desires the distribution.

However, in the clinical-path management server of JP2008-059316A, there is a problem in that a function of managing the data after the creation of the second opinion is complicated. This is because the second opinion is created as separate data from the clinical path. Therefore, it is necessary for the clinical-path management server to have a configuration for managing the data of a second opinion having a different data format, in addition to a configuration for managing data of the clinical path.

Further, for example, a display format changing process for changing a display format of the second opinion data into a display format of the clinical path is also necessary in order to display the second opinion and the clinical path in a format facilitating the contrasting since the data formats are different. In a case in which the display format changing process is performed, for example, a process of comparing data having different formats with each other and extracting data of the same item to be contrasted is necessary. In a case in which the data format is changed by the request destination, the display format changing process becomes more complicated in order to cope with a variety of data formats.

Further, for a second opinion requesting function, it is necessary for the clinical-path management server to have a function of attaching information on the clinical path to patient information or request information and transmitting the result information when performing the request with respect to a request destination. This clinical path attachment function also causes complication of a configuration. Since the clinical-path management server is originally a server that manages data of the clinical path, costs or time and efforts for modification should be minimized when additional functions such as the second opinion requesting function are added.

SUMMARY OF THE INVENTION

An object of the present invention is to provide a clinical-path management server and a clinical-path management system capable of performing a request for a second opinion or data management without complicating a configuration.

To achieve the above object, a clinical-path management server of the present invention includes a clinical path database, an authority management information storage unit, an access request reception unit, an authentication processing unit, a second opinion acquisition request reception unit, a creation request issuance unit, and an authorization unit. The clinical path database stores a clinical path in which medical care information on a schedule and a record of medical care of a patient is recorded in time-series so that the clinical path is searchable. The authority management information storage unit stores authority management information in which an access authority to access the clinical path data is recorded. The access request reception unit receives a request for access to the clinical path database and performs input and output of the clinical path. The authentication processing unit performs an authentication process of a request source based on the authority management information upon receiving the request for access. The second opinion acquisition request reception unit receives an acquisition request for a second opinion which is an opinion of a second doctor other than a first doctor involved in creation of the clinical path. The creation request issuance unit issues a creation request for the second opinion to the second doctor upon receiving the acquisition request. The authorization unit updates the authority management information at the time of issuing the creation request, to grant an editing authority to edit the clinical path of the patient who is a target of the second opinion to the second doctor as a request destination of the second opinion.

It is preferable that, for the clinical path in which the editing authority is granted to the second doctor, backup data of the clinical path before editing is stored in the clinical path database.

It is preferable for the creation request issuance unit to notify the second doctor of the creation request issued to an address of the second doctor. Further, it is preferable for the authentication information necessary for the authentication process is included in the creation request.

It is preferable for the authorization unit to record the authentication information in the authority management information at the time of granting the editing authority. Further, it is preferable for the authorization unit to determine a time limit and grant the editing authority.

It is preferable for the access request reception unit to append, to the clinical path, that the second opinion is being requested upon issuance of request information of the second opinion. Further, it is preferable for the clinical-path management server to further include a notification unit that notifies at least one of the patients and the first doctor that creation of the second opinion has ended.

A clinical-path management system of the present invention includes a clinical-path management server and a terminal adapted to access the clinical-path management server. The clinical-path management server includes a clinical path database, an authority management information storage unit, an access request reception unit, an authentication processing unit, a second opinion acquisition request reception unit, a creation request issuance unit, and an authorization unit.

According to the present invention, it is possible to provide a clinical-path management server and a clinical-path management system capable of performing a request for a second opinion or data management without complicating a configuration.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

Figure 1:
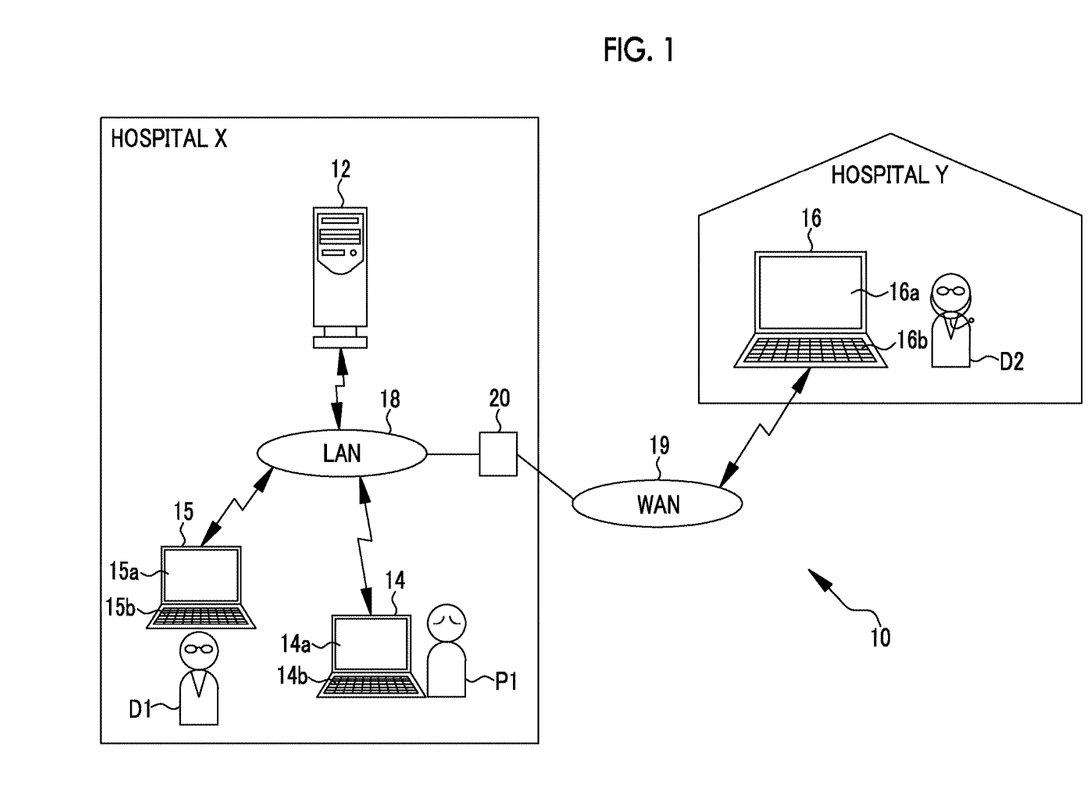
FIG. 1 is a schematic diagram of a clinical-path management system of the present invention.

As illustrated in FIG. 1, a clinical-path management system (hereinafter referred to as a clinical path (CP) management system) 10 includes a clinical-path management server (hereinafter referred to as a CP management server) 12, and a terminal capable of accessing the clinical-path management server 12. The accessible terminal includes a patient terminal 14 used by a patient P1, an attending doctor terminal 15 used by an attending doctor D1 of the patient P1, and a second opinion attending doctor terminal (hereinafter referred to as an SO attending doctor terminal) 16 used by a second opinion attending doctor (hereinafter referred to as an second opinion (SO) attending doctor) D2. The CP management server 12, the patient terminal 14, and the attending doctor terminal 15 are all installed in hospital X, and are connected to each other to be able to perform information communication by a local area network (LAN) 18 which is an in-hospital network in hospital X.

The SO attending doctor terminal 16 is provided in hospital Y and connected to the LAN 18 over a wide area network (WAN) 19. The CP management server 12 has a function of requesting the SO attending doctor D2 of hospital Y who is a second doctor other than the attending doctor D1 of hospital X to provide a second opinion for medical care content of the patient P1. Therefore, the SO attending doctor terminal 16 is allowed to access the CP management server 12 over the LAN 18 and the WAN 19 under certain conditions. A router 20 for connecting the LAN 18 to the WAN 19 is provided between the LAN 18 and the WAN 19.

The patient terminal 14, the attending doctor terminal 15, and the SO attending doctor terminal 16 are, for example, personal computers, have displays 14a, 15a, and 16a, and input units 14b, 15b, and 16b, respectively. The patient terminal 14, the attending doctor terminal 15, and the SO attending doctor terminal 16 have software such as an operating system or a WEB browser installed therein, and can access the CP management server 12 through the WEB browser. The displays 14a, 15a, and 16a display various screens distributed from the CP management server 12. The input units 14b, 15b, and 16b input an operation signal and, for example, transmit operation instructions for the respective terminals 14, 15, and 16 or various requests for the CP management server 12 through the WEB browser. For each of the input units 14b, 15b, and 16b, for example, a mouse or a keyboard is used.

For example, a desktop computer or a notebook computer having a communication function is used as the patient terminal 14, the attending doctor terminal 15, and the SO attending doctor terminal 16. Of course, various mobile terminals having a wireless function such as a smart phone (advanced mobile phone) or a personal digital assistant (PDA) may be used. In a case in which the mobile terminal is used, the mobile terminal is connected to the LAN 18 via an access point which is a wireless repeater. Although not illustrated, there are, in hospital X, terminals of medical staffs of hospital X such as nurses or clerical staffs, in addition to the patient terminal 14 or the attending doctor terminal 15. These terminals can access the CP management server 12.

The WAN 19 may be a network which connects the SO attending doctor terminal 16 to the LAN 18 so that the SO attending doctor terminal 16 can perform communication with the LAN 18 and may be, for example, the Internet, a dedicated line, a mobile telephone line, a public wireless LAN, or the like, or a combination thereof. The SO attending doctor terminal 16 can communicate with the CP management server 12 over the WAN 19. In a case in which the public network is used as the WAN 19, the SO attending doctor terminal 16 and the LAN 18 are connected to, for example, a virtual private network (VPN) such that information leakage is prevented.

The router 20 is a repeater for connecting the LAN 18 to the WAN 19. A firewall or the like which prevents unauthorized access to the LAN 18 from the outside may be provided between the LAN 18 and the WAN 19. Accordingly, information leakage or information falsification of the CP management server 12 or the like can be more reliably prevented.

Figure 2:
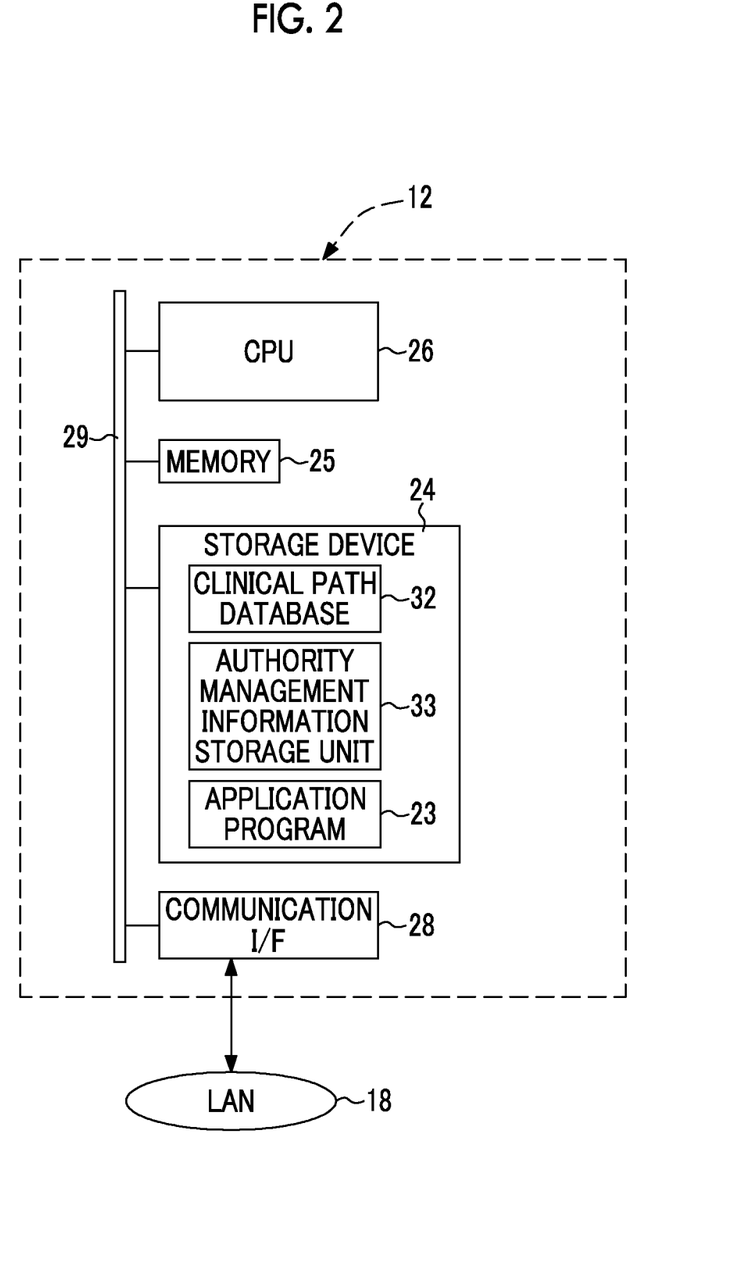
FIG. 2 is a configuration diagram of a clinical-path management server.

As illustrated in FIG. 2, the CP management server 12 is configured by installing an application program (AP) 23 for operating the CP management system 10 based on a personal computer or a workstation. A storage device 24, a memory 25, a central processing unit (CPU) 26, and a communication I/F (Inter-Face) 28 are provided in the CP management server 12, and are connected to each other via a data bus 29.

The storage device 24 is a device for storing various data and includes, for example, a hard disk drive. In the storage device 24, a clinical path database (hereinafter referred to as CP DB) 32 and an authority management information storage unit 33 are stored, in addition to an AP 23, such as a control program or software for a CP system.

The memory 25 is a work memory used for the CPU 26 to execute a process. The CPU 26 loads the AP 23 stored in the storage device 24 into the memory 25 and executes the process according to the program to generally control each unit of the computer.

The communication I/F 28 is a communication unit for connection with the LAN 18. The communication I/F 28 communicates with the patient terminal 14, the attending doctor terminal 15, and the SO attending doctor terminal 16 over the LAN 18.

The CP management server 12 receives various requests such as an information distribution request from the patient terminal 14, the attending doctor terminal 15, and the SO attending doctor terminal 16 via the communication I/F 28, accepts the received request, and executes a process according to content of the request.

Figure 3:
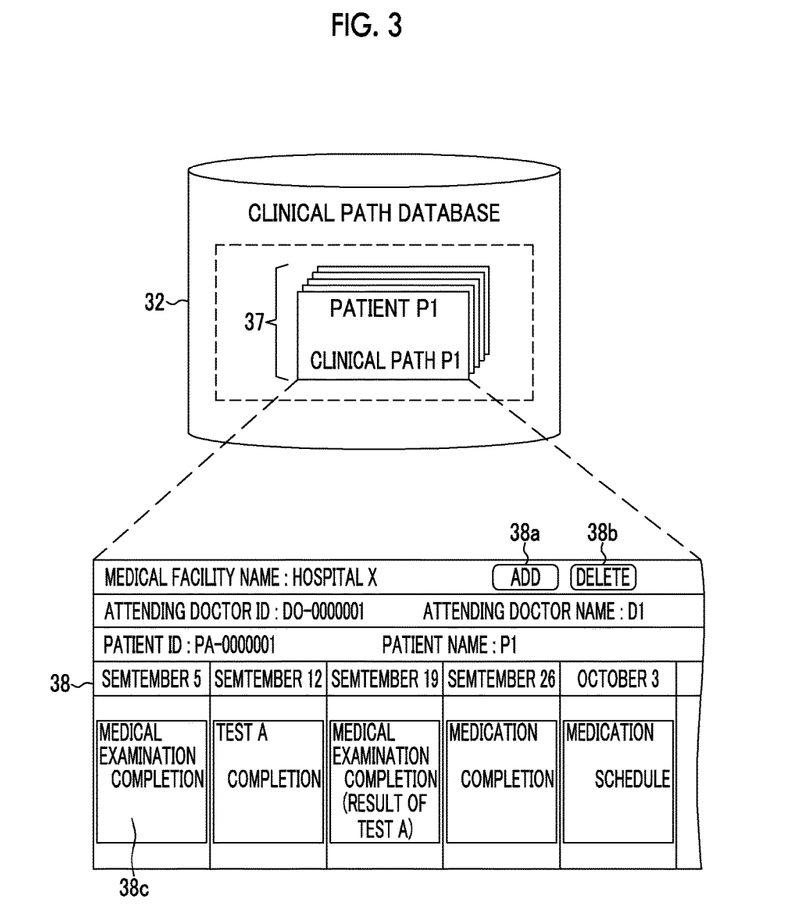
FIG. 3 is an illustrative diagram of a clinical path database.

As illustrated in FIG. 3, clinical path data (hereinafter referred to as CP data) 37 including a plurality of clinical paths for each patient is stored in the CP DB 32. CP data 37 is displayed, for example, in a display mode shown as a CP 38 in the patient terminal 14 and the attending doctor terminal 15.

The CP 38 is medical care schedule data in which medical care information on a schedule and a record of medical care (diagnosis and treatment) performed on the patient in hospital X is recorded in time series. The medical care information includes a schedule of medical care activity such as medical examination, test, surgery, or medication, and results or records of the medical care activity such as a test result, a medical examination record, and a medication result. Further, since the clinical path is information created for each patient, patient information such as a patient Identification Data (ID), a patient name, an age, and a gender, a name or an ID of the attending doctor D1 responsible for the patient, and the like are recorded in the clinical path. Here, the attending doctor D1 corresponds to a first doctor involved in creation of the clinical path, and the SO attending doctor D2 corresponds to a second doctor.

The CP management server 12 distributes the CP data 37 to each of the terminals 14 and 15 in response to the distribution request from the patient terminal 14 and the attending doctor terminal 15. In each of the terminals 14 and 15, the received CP data 37 is displayed in the display format of the CP 38 by the WEB browser, and the patient P1 or the attending doctor D1 can view the CP 38. Further, in a case in which the CP data 37 is newly created by the attending doctor D1 or editing is performed on the CP data 37 in the attending doctor terminal 15, the CP management server 12 receives the newly created or edited CP data 37 from the attending doctor terminal 15, and updates the CP DB 32. Further, the CP management server 12 can grant a viewing and editing authority to the SO attending doctor D2 under certain conditions. Accordingly, in the SO attending doctor terminal 16 of the SO attending doctor D2, the CP 38 can also be viewed and edited.

In the CP 38, various medical care information is displayed on each date on which a medical care event (for example, medical examination, test, or medication) is performed according to a schedule. In each field, a display showing whether or not the medical care event has been performed is performed. For example, respective medical care event display fields with date such as September 5, September 12, September 19, September 26, and October 3 are provided. Medical care events such as medical examination completion, test A completion, medical examination completion (result of test A), medication completion, and medication schedule are displayed in the respective display fields. Here, the medical care event written as completion indicates that the medical care event has been performed, and the medical care event written as a schedule indicates that the medical care event has not been performed and has been scheduled. On the display screen of the CP 38, an addition button 38a for adding a medical care event, and a deletion button 38b for deleting a medical care event are provided. Further, an event button 38c is provided for each medical care event.

Figure 4:
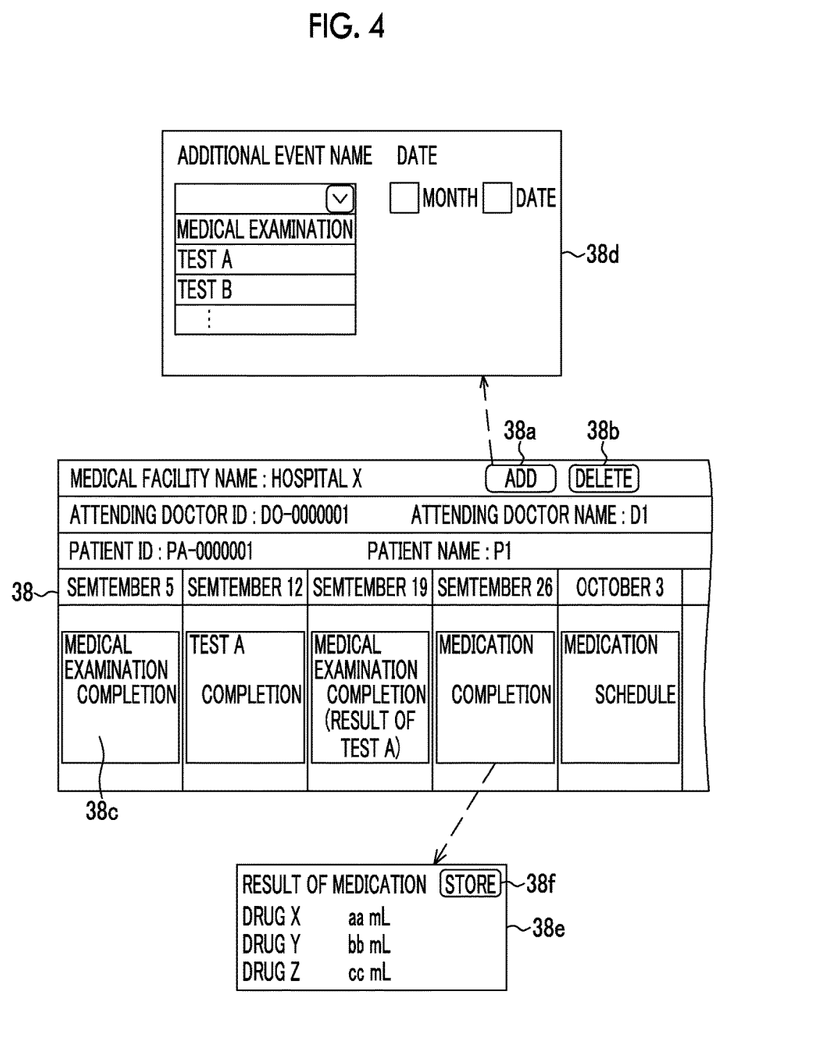
FIG. 4 is an illustrative diagram of a clinical path.

As illustrated in FIG. 4, if the addition button 38a is selected on the display screen of the CP 38, an item addition screen 38d is popped up and displayed. In the item addition screen 38d, respective spaces for selecting or inputting an additional event name and a date are provided. By selection or input of these, a desired medical care event is added in a desired date field. On the other hand, when a deletion button 38b is selected, the display screen of the CP 38 enters a medical care event deletion mode. By selection of the event button 38c, a medical care event desired to be deleted is deleted from the CP 38.

If the event button 38c is selected, a detailed display screen 38e in which details of a medical care event are displayed is popped up and displayed. By editing of the detailed display screen 38e, detailed information of the medical care event is edited. Further, by selection of an editing storage button 38f provided in the detailed display screen 38e, content of the editing performed on the detailed display screen 38e is stored in the CP 38.

For example, if the event button 38c regarding the medical care event of medication completion on September 26 is selected, the detailed display screen 38e in which a result of medication in a week of September 26 is displayed is displayed. In the detailed display screen 38e in the medical care event of medication completion, details of a result of medicating drug X of aa mL, drug Y of bb mL, and drug Z of cc mL is displayed. While the example in which detailed content regarding the medication is displayed in the detailed display screen 38e has been shown in this example, a test image or the like is displayed in the detailed display screen 38e in a case in which image diagnosis such as X-ray test has been performed. There is an editing storage button 38f in an upper right portion of the detailed display screen 38e. If the editing storage button 38f is operated, content of the editing is stored. The content of the stored CP 38 is uploaded to the CP management server 12, and the CP data 27 in the CP DB 32 is updated.

Figure 5:
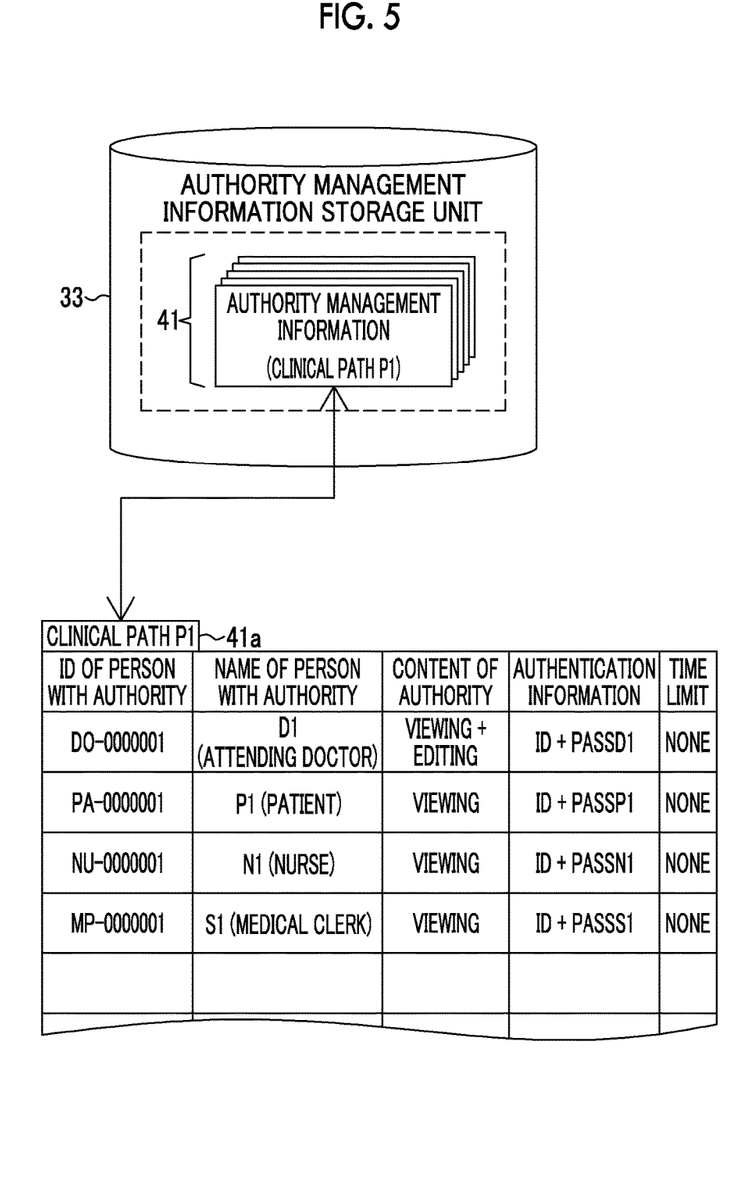
FIG. 5 is an illustrative diagram of authority management information.

As illustrated in FIG. 5, authority management information data 41 including a plurality of authority management information provided for each CP data 37 of each patient is stored in the authority management information storage unit 33. The authority management information is information for managing the access authority to the CP data 37. For example, information on the access authority to the CP 38 of the patient P1 is included in the authority management information 41a corresponding to the CP 38 of the patient P1 included in the authority management information data 41. An ID of a person with access authority, a name of a person with access authority, content of authority set for each person with access authority, authentication information, and a time limit of the access authority are included in the information of the access authority. The authentication information includes an authentication ID and a password.

For example, the attending doctor D1 of the patient P1, the patient P1, the nurse N1 who is responsible for care of the patient P1, and a medical clerk S1 who is responsible for medical affairs regarding medical care of the patient P1 are registered as persons with access authority to the CP 38 in the authority management information 41a. Editing authority is granted to the attending doctor D1, and only viewing authority is granted to the patient P1, the nurse N1, and the medical clerk S1. Here, it is understood that the viewing authority is included in the editing authority. A time limit is not provided in any access authority.

Figure 6:
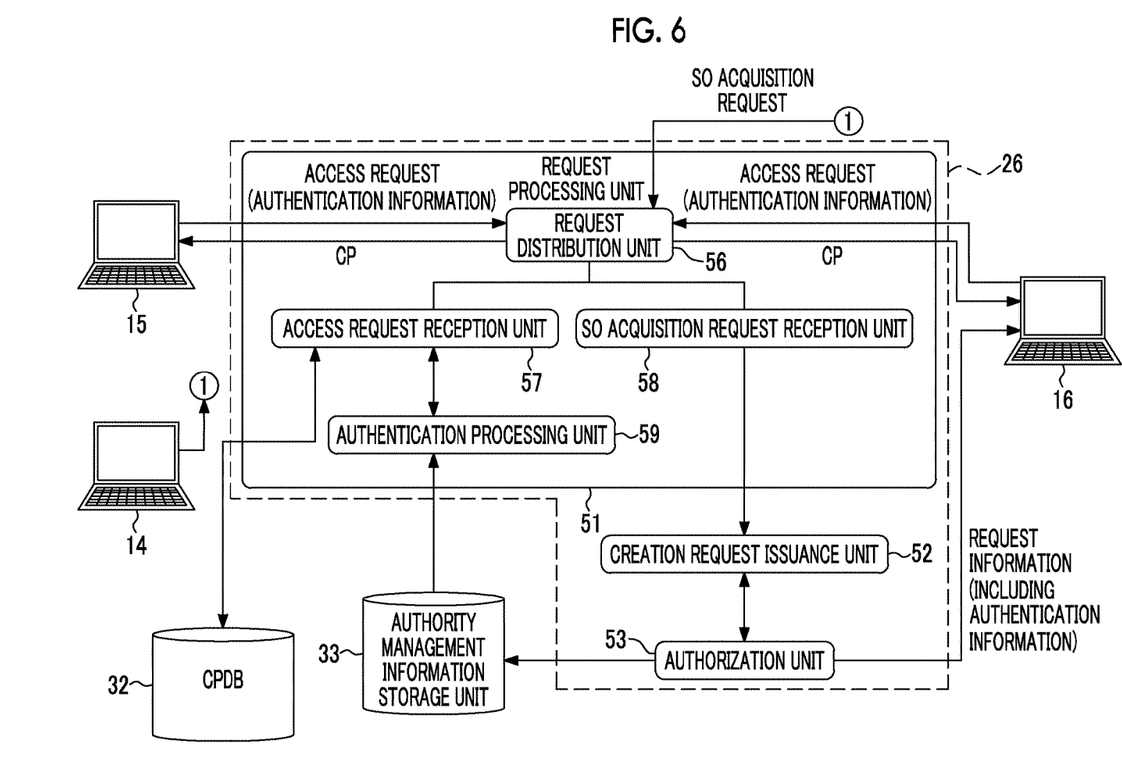
FIG. 6 is a functional schematic diagram of a clinical-path management server.

If the CPU 26 of the CP server 12 executes the AP 23, the CPU 26 functions as various functional units of the CP management system 10. In this case, the CPU 26 functions as a request processing unit 51, a creation request issuance unit 52, and an authorization unit 53, as illustrated in FIG. 6. The request processing unit 51 is a functional unit that receives various requests from the various terminals 14, 15, and 16 and executes a process according to the request, and includes a request distribution unit 56, an access request reception unit 57, a second opinion acquisition request reception unit (hereinafter referred to as an SO acquisition request reception unit) 58, and an authentication processing unit 59.

The request distribution unit 56 receives various requests from the various terminals 14, 15, and 16, and distributes the requests to various reception units. The various requests roughly include a request for access to the CP DB 32 and an SO acquisition request. The request for access to the CP DB 32 includes a distribution request to request the distribution in order to view or edit the CP data 37 in the CP DB 32, and an updating request to request updating of the CP data 37 in the CP DB 32 with CP data 37 newly created or edited by the attending doctor terminal 15 or the like. Further, the SO acquisition request is a request that is transmitted from the patient terminal 14 to the CP management server 12 in a case in which the patient P1 desires a second opinion.

Information for identifying content of the request is added to various requests as header information, and the request distribution unit distributes various requests by referring to the header information when the request distribution unit receives various requests. The access request is input to the access request reception unit 57, and the SO acquisition request is input to the SO acquisition request reception unit 58. Information for specifying the CP data 37 of an access target, such as a patient ID, is included in the access request, authentication information input at each terminal is attached, and the access request and the attached authentication information are also input to the access request reception unit 57.

When the access request reception unit 57 receives the request for access to the CP DB 32, the access request reception unit 57 sends the authentication information to the authentication processing unit 59. The authentication processing unit 59 accesses the authority management information storage unit 33 on the basis of the patient ID in the access request, and acquires authority management information corresponding to the CP data 37 of the patient ID of an access request target from the authority management information data 41. The authentication processing unit 59 compares the acquired authority management information with the authentication information and determines whether a request source has access authority according to content of the request for the CP data 37.

Specifically, in a case in which the request source has an access authority to the CP data 37 of the patient P1 or content of the request is a request for updating of the CP data 37, the authentication processing unit 59 determines, for example, whether or not a request source has editing authority. For example, in a case in which a request source ID and password do not match, the authentication processing unit 59 determines that the request source has no access authority. Further, even in a case in which it is determined that the request source has the access authority, the viewing authority is granted to the attending doctor D1, the patient P1, the nurse N1, and the medical clerk S1, and the editing authority is granted to only the attending doctor D1, in the authority management information 41a corresponding to the patient P1 illustrated in FIG. 5. Therefore, in the case of the request for updating of the CP data 37 from the attending doctor D1, the editing authority is determined to be present, and in other cases, the editing authority is determined to be not present. The authentication processing unit 59 sends a result of the determination to the access request reception unit 57.

In a case in which the access request reception unit 57 receives the determination result from the authentication processing unit 59 and the access request source has the access authority according to the requested content, the access request reception unit 57 permits the access. In a case in which the access request source does not have the access authority, the access request reception unit 57 rejects the request. For example, in a case in which the access request reception unit 57 permits a viewing request, the access request reception unit 57 reads the CP data 37 from the CP DB 32 and distributes the CP data 37. In a case in which the access request reception unit 57 permits an editing request, the access request reception unit 57 updates the CP data 37 in the CP DB 32 with CP data 37 uploaded from the terminal.

If the SO acquisition request reception unit 58 receives the SO acquisition request, the SO acquisition request reception unit 58 sends information on the patient P1 making the SO request, information on the SO attending doctor D2 designated as an SO request destination, and the requested content of the SO request to the creation request issuance unit 52. The creation request issuance unit 52 issues an SO creation request to the SO attending doctor terminal 16 used by the SO attending doctor D2. The SO creation request is sent to the authorization unit 53.

Figure 7:
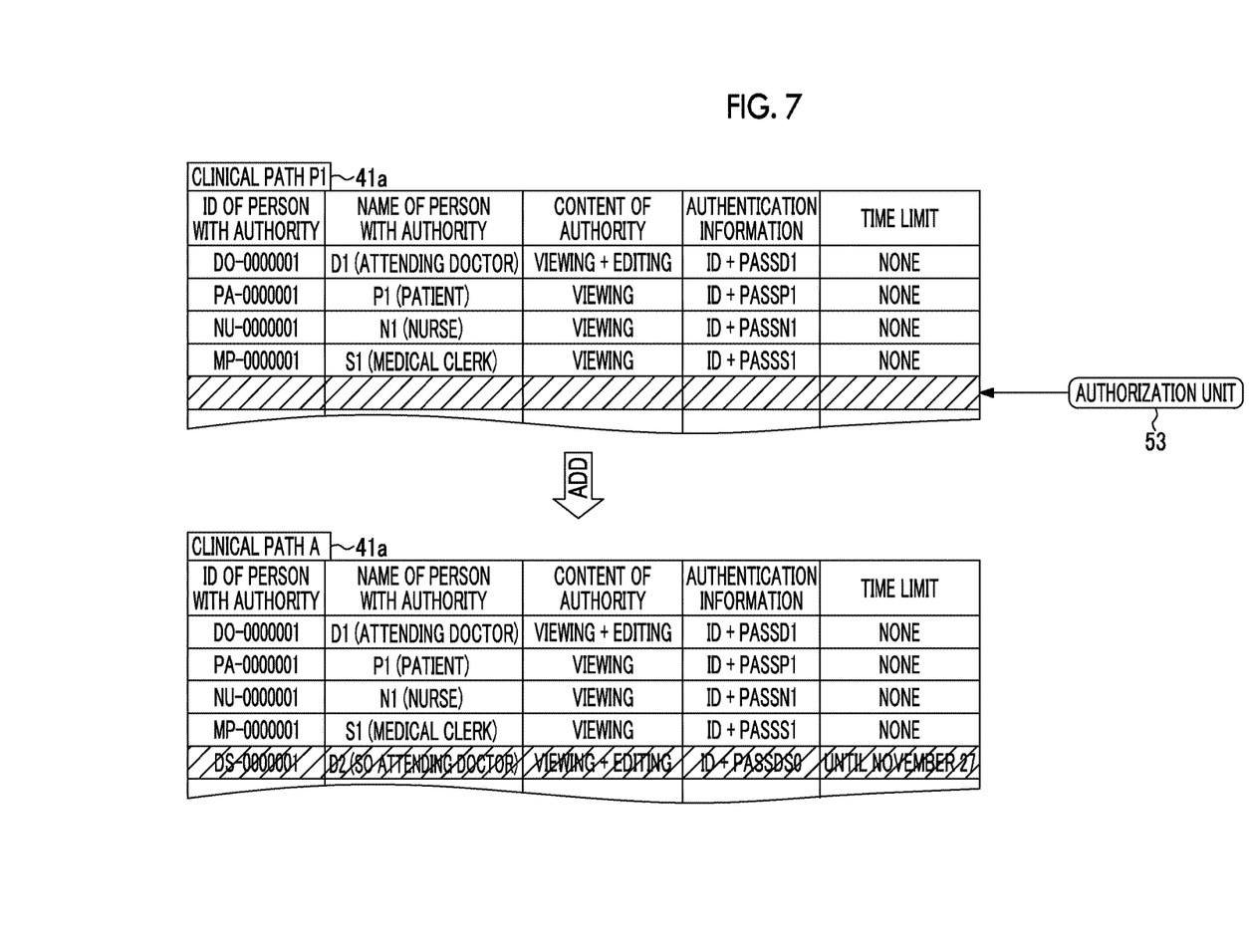
FIG. 7 is an illustrative diagram of an authorization unit.

If the authorization unit 53 receives the SO creation request from the creation request issuance unit 52, the authorization unit 53 provides the authentication information to the SO attending doctor D2, and transmits the authentication information and the request information on the SO request to the SO attending doctor terminal 16. Further, the authorization unit 53 accesses the authority management information storage unit 33, and adds the SO attending doctor D2 to the authority management information 41a on the CP data 37 of the patient P1 making the SO request, as illustrated in FIG. 7. The authorization unit 53 can also provide a time-limited authority and, for example, in FIG. 7, editing authority granted to the SO attending doctor D2 is valid until November 27. Further, a time limit of only the viewing authority and a time limit of the editing authority may be separately set.

Hereinafter, an operation of the above configuration will be described with reference to flowcharts illustrated in FIGS. 8 to 10. An entire processing flow in a case in which the CP management server 12 requests the SO attending doctor D2 to provide a second opinion in response to a request from the patient P1, and the SO attending doctor D2 creates the second opinion and uploads the created second opinion is as illustrated in FIG. 8.

Figure 8:
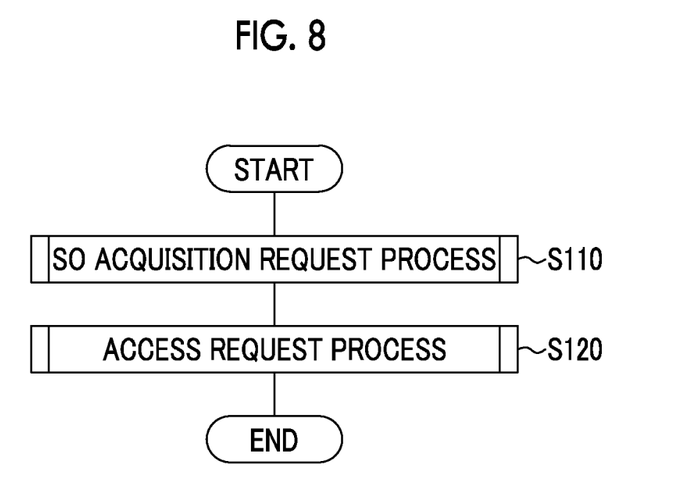
FIG. 8 is a flowchart illustrating an operation of the clinical-path management system.

In FIG. 8, an SO acquisition request process 5110 is a process in which the CP management server 12 receives an SO acquisition request from the patient P1 and requests the SO attending doctor D2 to create a second opinion.

The access request process 5120 is a process in which the SO attending doctor D2 receiving the request to create the second opinion accesses the CP management server 12, creates the second opinion on the basis of the distributed CP data 37, and uploads the edited CP data 37 to the CP management server 12.

Figure 9:
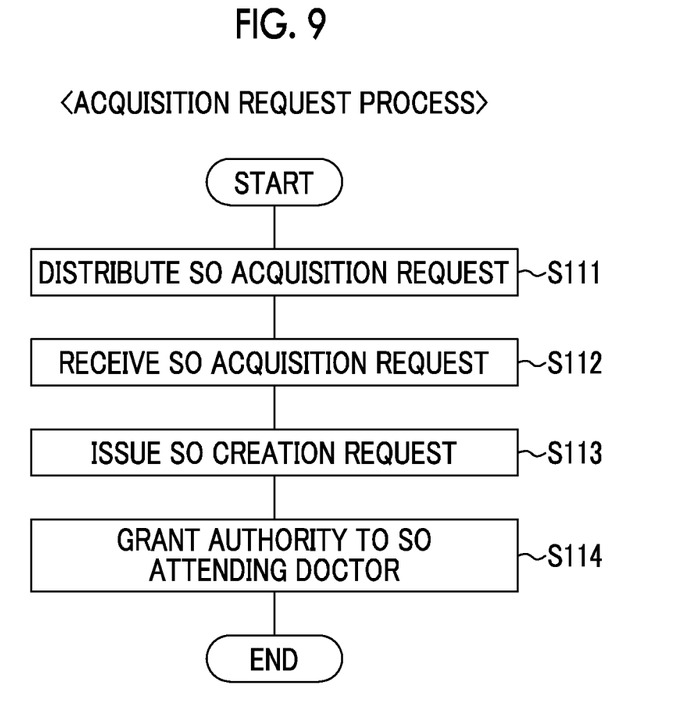
FIG. 9 is a flowchart of a second opinion acquisition request process.

The SO acquisition request process 5110 is executed in a procedure illustrated in FIG. 9. If the patient P1 transmits the SO acquisition request to the CP management server 12 through the patient terminal 14, the request distribution unit 56 distributes this SO acquisition request to the SO acquisition request reception unit 58 (SO acquisition request distribution process S111). The SO acquisition request reception unit 58 receives the SO acquisition request, and sends the fact that an SO request to the SO attending doctor D2 is received from the patient P1, to the creation request issuance unit 52 (SO acquisition request reception process S112). The creation request issuance unit 52 issues an SO creation request to the SO attending doctor terminal 16 and sends the SO creation request to the authorization unit 53 (SO creation request issuing process S113).

When the authorization unit 53 receives the SO creation request, the authorization unit 53 transmits authentication information of the SO attending doctor D2 and request information of the SO request to the SO attending doctor terminal 16. Further, the authorization unit 53 adds the SO attending doctor D2 to the authority management information 41a (authorization process S114). Here, a type of authority granted to the SO attending doctor D2 is set to editing authority. Accordingly, editing authority to edit the CP 38 of the patient P1 is granted to the SO attending doctor D2.

Figure 10:
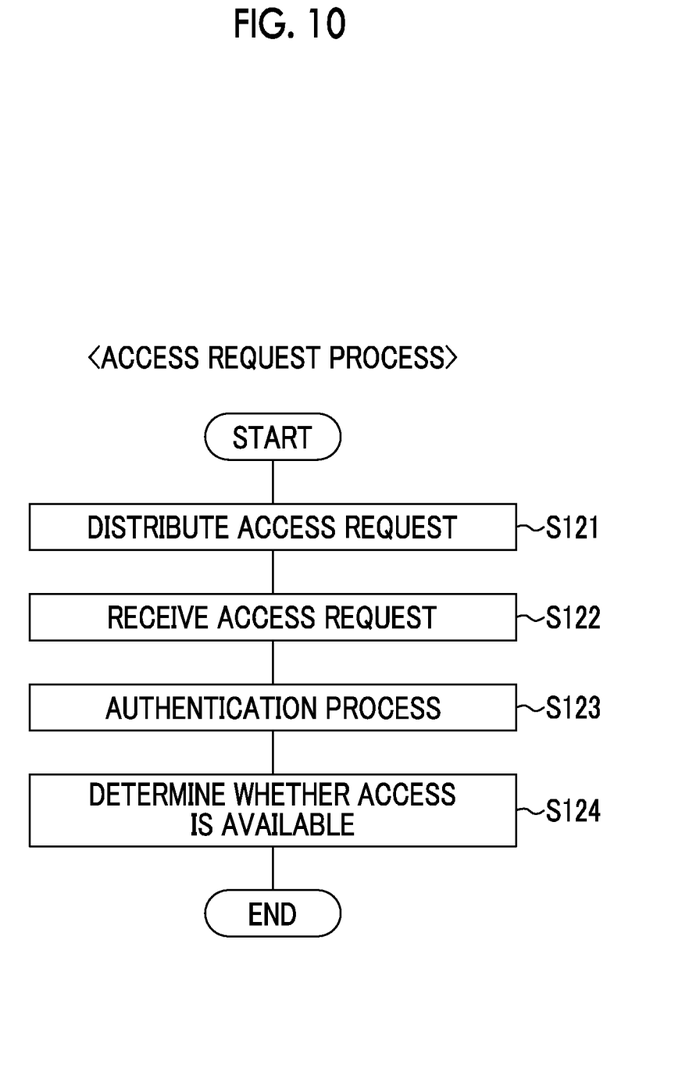
FIG. 10 is a flowchart of an access request process.

The access request process 5120 is executed in a procedure illustrated in FIG. 10. When the above-described SO acquisition request process is performed, the request information and the authentication information are transmitted to the SO attending doctor terminal 16. The SO attending doctor D2 receiving the SO creation request performs a request for access to the CP data 37 of the patient P1 from the SO attending doctor terminal 16 in order to create the second opinion regarding the patient P1. When the SO attending doctor terminal 16 accesses the CP management server 12, the SO attending doctor terminal 16 attaches the authentication information received from the authorization unit 53 in the SO acquisition process, to the access request, and performs the access to the CP management server 12.

The request distribution unit 56 distributes this access request to the access request reception unit 57 (access request distribution process S121). The access request reception unit 57 receives this access request, and inputs the request for access to the CP data 37 of the patient P1 from the SO attending doctor D2 and the authentication information to the authentication processing unit 59 (access request reception process S122).

The authentication processing unit 59 accesses the authority management information storage unit 33 to acquire the authority management information 41a on the CP data 37 of the patient P1. The authentication processing unit 59 compares the authority management information 41a with the authentication information and determines that the SO attending doctor D2 has been registered as a person with an access authority, who has editing authority (authentication process S123). The authentication processing unit 59 sends a result of this determination to the access request reception unit 57.

The access request reception unit 57 receives the determination result from the authentication processing unit 59, and distributes the CP data 37 of the patient P1 to the SO attending doctor terminal 16 for the SO attending doctor D2. The CP data 37 is displayed as the CP 38 on the WEB browser, in the SO attending doctor terminal 16. The SO attending doctor D2 views the CP 38 to confirm medical care content of medical examination, test, treatment, or the like of the patient P1, and a future medical care schedule. Based on the confirmed content, the SO attending doctor D2 creates a second opinion including an opinion of the SO attending doctor D2.

The SO attending doctor D2 edits the CP 38 and inputs content of the created second opinion. The SO attending doctor terminal 16 uploads the CP data 37 according to the edited CP 38 to the CP management server 12 to perform the request for updating of the CP data 37. The access request reception unit 57 of the CP management server 12 confirms that there is editing authority as a result of the authentication process, and updates the CP data 37 in the CP DB 32 with the uploaded CP data 37. Thus, the SO attending doctor D2 can view and edit the CP 38 of the patient P1 through the SO attending doctor terminal 16.

As described above, according to the present invention, it is possible to provide the CP management server 12 or the CP management system 10 capable of performing a request for the second opinion and the data management thereof without complicating the configuration. Specifically, a CP management server has a configuration in which the CP DB 32, the authority management information storage unit 33, the access request reception unit 57, and the authentication processing unit 59 in the CP management server 12 has no function of requesting the second opinion. By adding the configuration for granting editing authority to edit the CP data 37 to the SO attending doctor D2 to such a CP management server, the CP data 37 after editing becomes the second opinion data, and accordingly, the configuration for managing the second opinion data in a different format from the CP data 37 becomes unnecessary. Here, a configuration for granting editing authority to edit the CP data 37 to the SO attending doctor D2 includes the request distribution unit 56, the SO acquisition request reception unit 58, the creation request issuance unit 52, and the authorization unit 53. Accordingly, it is possible to perform a second opinion request or data management without complicating the configuration. Further, since the second opinion is created by the editing of the CP data 37, the second opinion is created in the same display format as the CP 38, and accordingly, contrasting with the CP 38 before the creation is easy.

Further, an address of the CP management server 12, an access ID, a password, or the like is used as the authentication information, and is the same as in a scheme of granting a normal access authority to doctors or nurses. Therefore, the CP management server 12 of the present invention can be obtained through a small modification without complicating a structure of the CP management server.

Further, a time limit may not be provided in the authority granted to the SO attending doctor D2, but it is preferable for the authority to be time-limited, as in this embodiment. With the time limit, the access authority can be granted to the SO attending doctor D2 by a necessary period of time. Therefore, it is possible to prevent the SO attending doctor D2 from accessing the CP data 37 of the patient P1 after it is not necessary to access the CP data 37 of the patient P1. Accordingly, it is possible to hold security of the CP management server 12.

For time limits of the authorities, time limits of the viewing authority and the editing authority may be separately set. For example, the time limit of the editing authority is approximately two weeks, whereas the time limit of the viewing authority is approximately one month. The viewing authority may be set to be relatively longer. Accordingly, the SO attending doctor D2 can confirm how his or her second opinion is utilized for subsequent treatment or the like of the attending doctor D1 after editing, and the SO attending doctor D2 can strive to improve quality of medical service including a future second opinion.

Further, for the CP data 37 of the patient P1 edited by the SO attending doctor D2, it is preferable to have a function of storing, in the CP DB 32, the data of the CP data 37 before editing is performed by the SO attending doctor D2, as backup data. Accordingly, it possible to reliably preserve the CP data 37. Further, for the editing authority granted to the SO attending doctor D2, an editable range may be limited. For example, the SO attending doctor D2 may not have editing authority to edit basic information such as patient information or attending doctor information, or a medical care event before the SO creation request is received. Thus, it is possible to preserve the CP data 37 more reliably. Further, it is possible to display the CP data 37 before and after editing so that the data can be contrasted with each other, by storing the backup data.

Further, while the example in which the SO attending doctor terminal 16 is notified of the SO creation request issued by the creation request issuance unit 52 has been described in the above embodiment, an address other than the SO attending doctor terminal 16, such as a mail address of a mobile phone of the SO attending doctor D2, may be notified of the issued SO creation request. Further, a plurality of addresses such as both of the SO attending doctor terminal 16 and the mobile phone may be notified of the SO creation request. Accordingly, the SO attending doctor D2 can quickly recognize the SO creation request.

Figure 11:
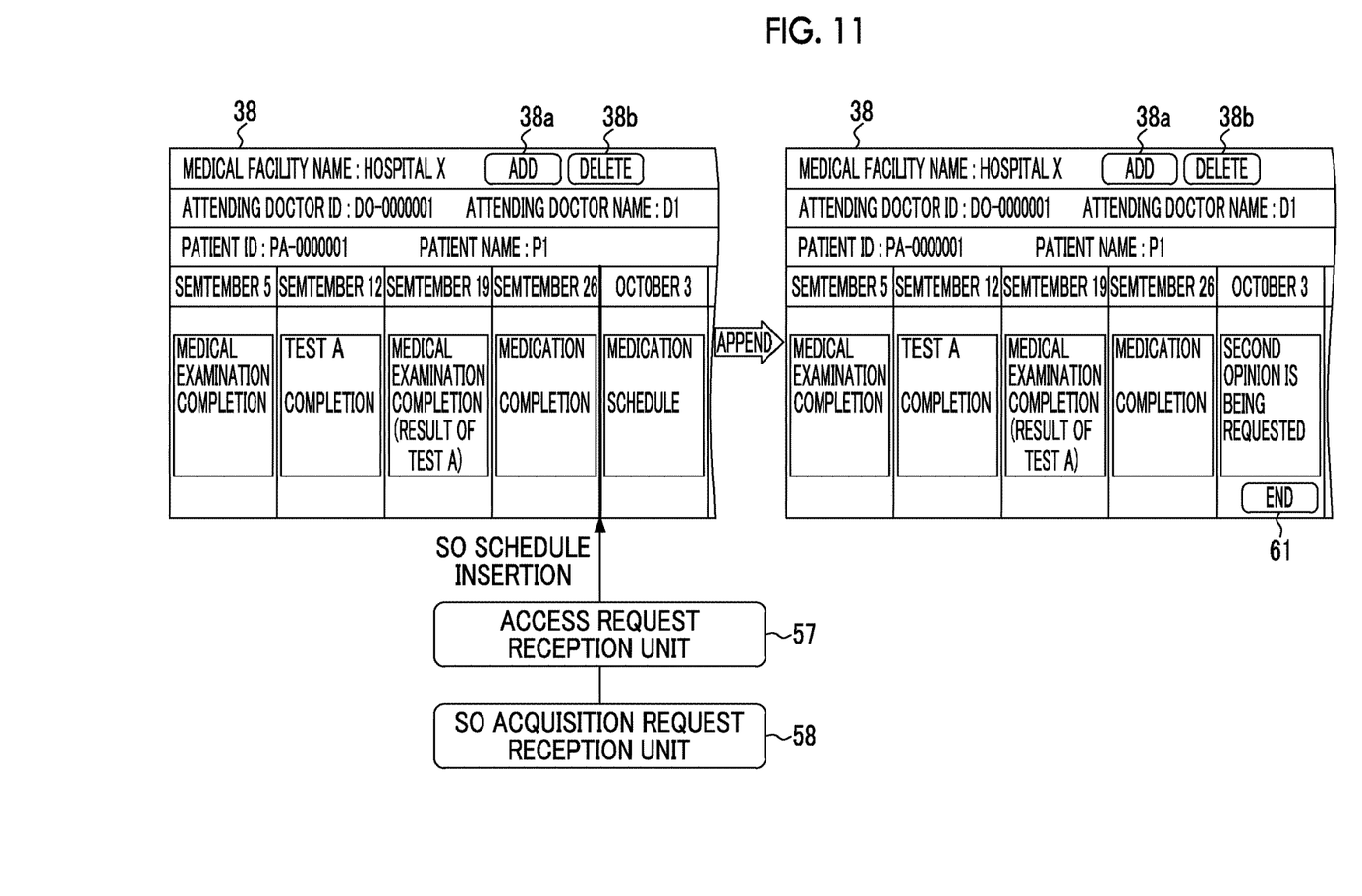
FIG. 11 is an illustrative diagram of a function of inserting a second opinion schedule and a function of ending second opinion creation.

Further, when the SO acquisition request reception unit 58 receives the SO acquisition request, the SO acquisition request reception unit 58 may send the fact that the SO request to the SO attending doctor D2 is received from the patient P1, to the access request reception unit 57. The access request reception unit 57 can receive the fact and append the fact that the SO request is being made, to the CP data 37 of the patient P1. For example, the access request reception unit 57 writes "SO request is being made" to a field corresponding to an SO request period of the CP 38, as illustrated in FIG. 11. Accordingly, the attending doctor D1 can view the CP 38 of the patient P1 and recognize that the patient P1 is making the SO request. Further, the patient P1 can view his or her CP 38 and recognize that the SO acquisition request had been received.

Further, as illustrated in FIG. 11, a second opinion creation end button (hereinafter referred to as an SO creation end button) 61 for inputting the fact that the SO attending doctor D2 has ended the SO creation may be displayed on the CP 38 when the SO attending doctor D2 has ended the SO creation. When the SO creation end button 61 is selected by the SO attending doctor D2, the CP management server 12 detects that the creation of the second opinion had ended. Further, it is preferable to include a notification unit that notifies the patient P1 making the SO acquisition request or the attending doctor D1 of the patient P1 that the creation of the second opinion had ended when the CP management server 12 has detected that the SO creation has ended. The CPU 26 of the CP management server 12 functions as the notification unit. In a case in which the CPU 26 detects that the creation of the second opinion has ended, the CPU 26 notifies a pre-registered notification destination (for example, e-mail address) of the patient P1 or the attending doctor D1 that the creation of the second opinion had ended.

From this notification, the patient P1 or the attending doctor D1 can rapidly recognize the end of the creation of the second opinion and can immediately confirm the second opinion. Further, such notification may be performed each time the CP data 37 of the CP DB 32 is updated. With this configuration, the patient may refer to SO from a CP screen at any time. The notification destination may be both of the patient P1 and the doctor D1 or may be one of the patient P1 and the doctor D1.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A clinical-path management server comprising:
   a memory;
   a clinical path database that stores a clinical path in which medical care information on a schedule and a record of medical care of a patient is recorded in time-series so that the clinical path is searchable;
   an authority management information storage that stores authority management information in which an access authority to access the clinical path data is recorded;
   a processing circuitry configured to perform functions of:

receiving a request for access to the clinical path database and performs input and output of the clinical path;

performing an authentication process of a request source based on the authority management information upon receiving the request for access;

receiving an acquisition request for a second opinion which is an opinion of a second doctor other than a first doctor involved in creation of the clinical path;

issuing a creation request for the second opinion to the second doctor upon receiving the acquisition request; and updating the authority management information at the time of issuing the creation request, to grant an editing authority to edit the clinical path of the patient who is a target of the second opinion to the second doctor as a request destination of the second opinion.

2. The clinical-path management server according to claim 1,
wherein, for the clinical path in which the editing authority is granted to the second doctor, backup data of the clinical path before editing is stored in the clinical path database.

3. The clinical-path management server according to claim 2,
wherein the creation request issuance unit notifies the second doctor of the creation request issued to an address of the second doctor.

4. The clinical-path management server according to claim 2,
wherein authentication information necessary for the authentication process is included in the creation request.

5. The clinical-path management server according to claim 4,
wherein the authorization unit records the authentication information in the authority management information at the time of granting the editing authority.

6. The clinical-path management server according to claim 5,
wherein the authorization unit determines a time limit and grants the editing authority.

7. The clinical-path management server according to claim 1,
wherein the access request reception unit appends, to the clinical path, that the second opinion is being requested upon issuance of request information of the second opinion.

8. The clinical-path management server according to claim 1, further comprising:
a notification unit that notifies at least one of the patient and the first doctor that creation of the second opinion has ended.

9. A clinical-path management system including a clinical-path management server and a terminal adapted to access the clinical-path management server, the clinical-path management server comprising:

a memory;

a clinical path database that stores a clinical path in which medical care information on a schedule and a record of medical care of a patient is recorded in time-series so that the clinical path is searchable;

an authority management information storage that stores authority management information in which an access authority to the clinical path data is recorded;

a processing circuitry configured to perform functions of:

receiving a request for access to the clinical path database and performs input and output of the clinical path;

performing an authentication process of a request source based on the authority management information upon receiving the request for access;

receiving an acquisition request for a second opinion which is an opinion of a second doctor other than a first doctor involved in creation of the clinical path;

issuing a creation request for the second opinion to the second doctor upon receiving the acquisition request; and updating the authority management information at the time of issuing the creation request, to grant an editing authority to edit the clinical path of the patient who is a target of the second opinion to the second doctor as a request destination of the second opinion.

* * * * *